United States Patent [19]

Zahn et al.

[11] 4,109,385
[45] Aug. 29, 1978

[54] METHOD OF STIPPLING, AND STIPPLING MANDREL THEREFOR

[75] Inventors: Eric H. Zahn, Bellevue; Philip W. Martin, Seattle, both of Wash.

[73] Assignee: Sterndent Corp., Old Greenwich, Conn.

[21] Appl. No.: 715,650

[22] Filed: Aug. 19, 1976

[51] Int. Cl.$^2$ .......................... A61C 3/06; B26D 1/12
[52] U.S. Cl. .......................................... 32/59; 279/83
[58] Field of Search ............... 32/40 R, 58, 59, 26, 32/29, 42, 46, 48, 49; 279/83; 51/170 PT, 170 T, 206 R

[56] References Cited

U.S. PATENT DOCUMENTS

| 706,013 | 8/1902 | Boyce | 32/59 |
|---|---|---|---|
| 3,371,452 | 3/1968 | Mabey | 51/206 R |
| 3,619,152 | 11/1971 | Yalof | 51/206 R |

*Primary Examiner*—Louis G. Mancene
*Assistant Examiner*—Mickey Yu
*Attorney, Agent, or Firm*—Ford E. Smith

[57] ABSTRACT

A rotatable mandrel is provided for stippling various surfaces, including the surface of plastic material, and is disclosed as comprising a cluster of burrs symmetrically arranged about the axis of rotation of the mandrel.

3 Claims, 8 Drawing Figures

METHOD OF STIPPLING, AND STIPPLING MANDREL THEREFOR

BACKGROUND OF THE INVENTION

The method of this invention and the stippling mandrel or tool of which performs the method will be described as it pertains to dental techniques, a field of use in which it typically finds worthwhile application. It is unintended thereby to restrict this invention to the stated particular and exemplary field of use, as those skilled in the pertinent art will readily recognize other fields of application for this invention.

In the production of dentures it is common practice to form of acrylic material a saddle-like element which straddles the toothless ridge of a jaw or a portion thereof. This element forms the base for replacement teeth. Usually a buccal portion of the acrylic base material is visible from outside the mouth. To make this skirt-like buccal portion realistic, it is colored and textured to provide a life-like appearance. Texturing to simulate flesh is sometimes accomplished to a degree during molding of the plastic material. That is, the mold is carved or shaped and roughened to approximate the natural flesh appearance. However, when the acrylic material is removed from the mold, it usually has a too-smooth, glossy and light-reflective surface that generally signals its artificial nature to viewers. It is desirable to dull the acrylic surface. Stippling is one practiced but time-consuming process to provide the desired appearance. In the past some stippling has been accomplished with a burr which has been bent out of its shank axis. The burr is eccentrically rotated and caused to strike or impact the plastic surface. The cutters of the burr are intended to remove minute particles of the plastic surface to produce the dulled surface appearance. Such may be accomplished with a highly skilled craftsman employing extreme care. However, such an eccentric tool can all too easily scar or gouge the plastic surface, removing too large or too long particles, producing unsightliness or necessitating repair.

It has been the principal object of this invention to teach a method and disclose a stippling tool in mandrel form which is easy to practice and use by relatively unskilled cratfsmen; that will rapidly produce over a large surface a dulled stippled effect without unsightly scarring or gouging; that is readily adjusted to present sharpened burr cutters to the work surface and which may be readily replaced; that avoids the hazards of the prior eccentric stippling tools; and that is inexpensive to make and to equip with burr cutters. These and other advantages and objects of the invention will become apparent from the following detailed description taken in reference to the drawings accompanying this application.

DESCRIPTION OF THE INVENTION:

The stippling tool comprises a body 10 having a cylindrical cavity 12 at its working end 14 and a shank 16 at its other or rear end.

Figure 1:
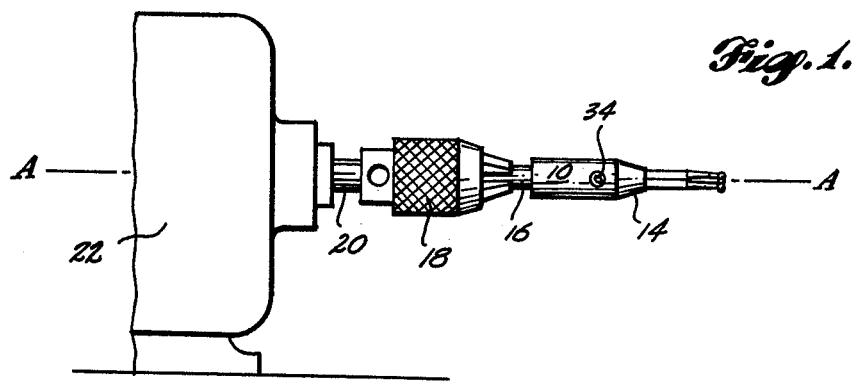
FIG. 1 shows a stippling mandrel mounted on an electric motor.
Figure 2:
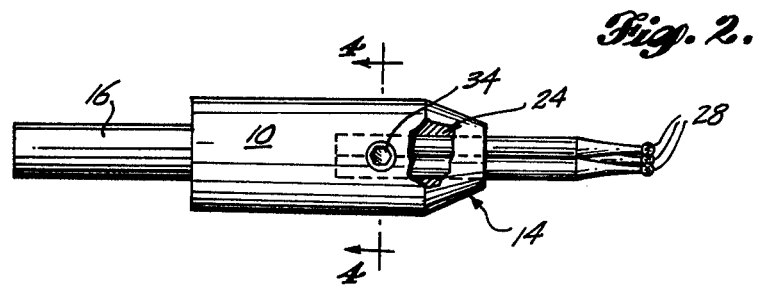
FIG. 2 is an enlarged side view of a stippling mandrel or tool.

Shank 10 is usually securely gripped in chuck 18 on shaft 20 of motor 22 whereby the body is forcibly rotated, preferably in a horizontal axis A—A as shown in FIG. 1.

Figure 5:
FIG. 5 shows a burr.
Figure 6:
FIG. 6 is an enlarged end view of a burr showing its cutters.

Referring to FIG. 5, burr 23 having shank 24 having neck 26 supports on its operating end the cutter head 28. In FIG. 6 is shown much enlarged a typical cutter head 28 comprising a hub body 30 and plural cutters 32 outstanding therefrom. It is desirable that cutter head 28 be no larger than the diameter of shank 24 for reasons to be later discussed.

Figure 4:
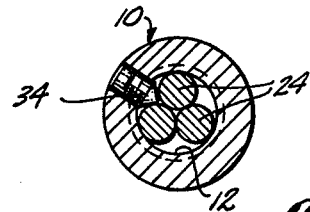
FIG. 4 is a cross-section view on line 4—4 of FIG. 2.

A cluster of burrs 23 is inserted into cavity 12 substantially filling the same, as can be seen in cross-section in FIG. 4. In such assembly the burr shanks 24 of the cluster are in side-by-side relation. Each has line contact with the wall of cavity 12, and each has surface contacts with the adjacent other shanks of the cluster.

The cluster of cutters is secured tightly in cavity 12 by means of a screw 34 threadedly mounted in the cavity wall. The inner end of screw 34 is introduced into the vee-shaped interstice between a pair of shanks 24 and, when tightened, jams the several shanks against each other and tightly against the cavity wall.

Figure 7:
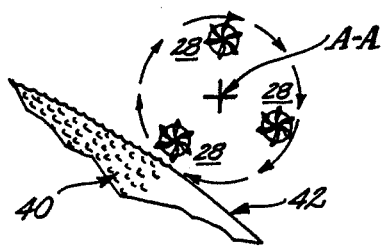
FIG. 7 is a schematic view in enlarged scale showing the stippling operation.

There has thus been described the clustering of a plurality of burr shanks 24, 24, 24 and their disposition symmetrically about the axis A—A of rotation. The necked shanks 26 extend outward of body 10 substantially parallel to axis A—A and support cutter heads 28 which revolve about axis A—A in a circular or planetary pattern as illustrated in FIG. 7. Under such conditions a worker desiring to surface stipple an object 40 presents the same to the members of the rapidly revolving cluster of cutter heads. Only the outer cutters 32 impact on or strike the presented surface 42 of object 40. Each cutter excavates a minute portion of surface 42, thus in gross producing the stippled surface effect as the worker moves body 40 relative the cluster of cutters.

Because of the spaced-apart relation of the cutter heads 28 in their planetary pattern of revolution around axis A—A, there is a limiting action on the depth of cut a cutter 32 may make as it impacts surface 42. There is no tendency for the cutters to gouge or scarify the surface as the worker holds the object to the tool. The result is an evenly stippled surface that is dull, of low light reflectance and in dentures devoid of the shiny and unnatural appearance considered so undesirable.

While the cutters 32 are made of good tool steel and are hardened and tempered in good manner, long and extensive use will naturally result in dulling of those which are working, i.e., those at the outside of the planetary pattern. The cutter shanks 24 are locked by screw 34 in cavity 12 and the cutters 32 nearest the axis A—A are inoperable during use. Thus the worker, to quickly adjust the tool to present sharp cutters, need only loosen screw 34 and rotate each cutter head 28 about its own axis, retightening screw 34 when unused cutter edges 32 have been disposed outward.

Figure 3:
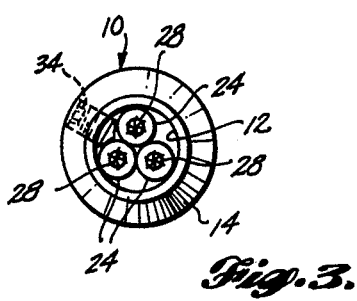
FIG. 3 is an end view of the stippling mandrel.
Figure 8:
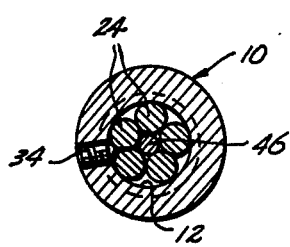
FIG. 8 is a cross-section similar to FIG. 4 but showing a five-burr cluster.

The use of the term "cluster" in reference to a tool having but three burrs is exemplary only. A cluster may comprise a larger number of burrs. Reference to FIG. 8 will disclose a cluster of burr shanks 24 there to comprise five in number. In such case a central void may remain which is there shown to be occupied by filler plug 46. Obviously, in a five-burr cluster the cutter heads will be more numerous and the spaces therebetween smaller than as shown with a three-burr cluster, as in FIG. 3.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the legitimate and valid scope of the appended claims, appropriately interpreted in accordance with the doctrine of equivalents.

What is claimed is:

1. A stippling mandrel, comprising:
   a tool body adapted to be chucked for rotational drive;
   said tool body having a cylindrical cavity extending axially inward at its outer end;
   a cluster of similar burr shanks coextensively inserted into and substantially filling said cavity in side-by-side relation, the dimensions of said cluster being such that each shank has line contact with the inner surface of said cavity and with the shanks adjacent thereto; and
   a screw threadedly mounted in the wall of said cavity and having an inner end penetrating said cavity and being disposed to bear in an interstice between an adjacent pair of shanks;
   each said shank having a burr on its outer end no larger than the diameter of said shank.

2. A tool according to claim 1 in which the cluster comprises three burr shanks.

3. A stippling tool, comprising:
   a rotational body securely supporting a cluster of dental-style burrs extending outward of said body in surrounding relation to the axis of rotation; said burrs being arranged within said body with longitudinal surface contact between the shanks of adjacent burrs, thus placing their respective cutting heads in a multi-sided pattern symmetrical of said axis; and
   means for rotating said body to cause said burrs to describe a circular path normal to said axis.

* * * * *